United States Patent
Hsu

(10) Patent No.: US 9,274,051 B2
(45) Date of Patent: Mar. 1, 2016

(54) MOVEMENT DETECTION DEVICE CAPABLE OF DETECTING THREE-DIMENSIONAL MOTIONS

(71) Applicant: PIXART IMAGING INC., Hsin-Chu County (TW)

(72) Inventor: En Feng Hsu, Hsin-Chu (TW)

(73) Assignee: PIXART IMAGING INC., Hsin-Chu County (TW)

( * ) Notice: Subject to any disclaimer, the term of this patent is extended or adjusted under 35 U.S.C. 154(b) by 142 days.

(21) Appl. No.: 14/109,347

(22) Filed: Dec. 17, 2013

(65) Prior Publication Data

US 2014/0151537 A1     Jun. 5, 2014

Related U.S. Application Data

(63) Continuation of application No. 12/987,333, filed on Jan. 10, 2011, now Pat. No. 8,633,462.

(51) Int. Cl.
*G01N 21/55* (2014.01)
*H04L 12/64* (2006.01)
*G06F 3/03* (2006.01)

(52) U.S. Cl.
CPC .............. *G01N 21/55* (2013.01); *G06F 3/0304* (2013.01); *H04L 12/6418* (2013.01)

(58) Field of Classification Search
CPC ... G01N 21/55; G06F 3/0304; H04L 12/6418
See application file for complete search history.

(56) References Cited

U.S. PATENT DOCUMENTS

| | | | |
|---|---|---|---|
| 6,657,705 B2 * | 12/2003 | Sano et al. | 356/4.01 |
| 6,683,969 B1 * | 1/2004 | Nishigaki et al. | 382/104 |
| 2007/0076843 A1 | 4/2007 | Matsumoto | |

* cited by examiner

*Primary Examiner* — Francis M Legasse, Jr.
(74) *Attorney, Agent, or Firm* — Hauptman Ham, LLP

(57) ABSTRACT

The present invention relates to a movement detection device for detecting a movement of an object in a space range. The movement detection device includes a light source, a light guiding element, at least two light sensing elements and a processing unit. The light sensing elements have an offset therebetween along a first direction such that the object, when moving in the space range, reflects the light from the light source sequentially to the light sensing elements through the light guiding element. The processing unit identifies the movement of the object along the first direction according to a sequence that the light sensing elements detect the light reflected by the object.

14 Claims, 4 Drawing Sheets

MOVEMENT DETECTION DEVICE CAPABLE OF DETECTING THREE-DIMENSIONAL MOTIONS

CROSS REFERENCE TO RELATED APPLICATION

This application is a continuation application of U.S. application Ser. No. 12/987,333, filed on Jan. 10, 2011, the disclosure of which is hereby incorporated by reference herein in its entirety. This application claims the priority benefit of Taiwan Patent Application Serial Number 099100506, filed on Jan. 11, 2010 and Taiwan Patent Application Serial Number 099115645, filed on May 17, 2010, the full disclosure of each of the above-listed prior applications is incorporated herein by reference.

BACKGROUND

1. Field of the Invention

This invention generally relates to a movement detection device that identifies three-dimensional motions of an object with a light source in combination with a plurality of light sensing elements.

2. Description of the Related Art

Current movement detection devices can only detect the movement substantially parallel to the movement detection device. For example, conventionally there is a cell phone including a movement detection device. If the cell phone is placed on a plane defined as an XY plane, the movement detection device of the cell phone can only detect an object moving along X and Y directions, e.g. a waving gesture along a direction substantially parallel to the cell phone. It is because that the sensor integrated in current movement detection devices is mainly for detecting whether an object blocks the sensor or not, and generally a plurality of sensors are integrated in a movement detection device to identify a moving direction of the object by detecting whether the movement of the object blocks the sensors and by recognizing a sequence that the plurality of sensors being blocked during operation. This kind of movement detection device is designed for detecting movements on a predetermined plane. For an object moving along a direction perpendicular to the predetermined plane (e.g. a Z-direction perpendicular to the XY plane), as the movement of the object does not change the projection of the object on the movement detection device, the conventional movement detection device can not effectively detect the motion of the object along a direction perpendicular to the predetermined plane.

Accordingly, a movement detection device that can simultaneously detect three-dimensional motions in a space range is required by the art.

SUMMARY

It is an object of the present invention to provide a movement detection device that may detect a movement of an object on a plane, which is substantially parallel to the movement detection device, and may detect a movement of the object along a direction perpendicular to the plane. By detecting the movement of the object on the plane, a specific command may be triggered to accordingly perform a post-processing and/or control mechanism according to the command. By detecting the movement of the object along a direction perpendicular to the plane, a distance variation of the object with respect to the movement detection device may be detected to trigger another specific command and to accordingly perform another post-processing and/or control mechanism according to the command.

It is an object of the present invention to provide a movement detection device that may define a three-dimensional space range in the space and may detect a motion of an object in the three-dimensional space range.

To achieve the above objects, the present invention provides a movement detection device configured to detect a movement of an object in a space range. The movement detection device includes a light source, a light guiding element, at least two light sensing elements and a processing unit. The light sensing elements have an offset therebetween along a first direction such that the object, when moving in the space range, reflects the light from the light source sequentially to the light sensing elements through the light guiding element. The processing unit identifies the movement of the object along the first direction according to a sequence that the light sensing elements detect the light reflected by the object.

The present invention further provides a movement detection device configured to detect a motion of an object. The movement detection device includes a light source emitting the light along an optical axis, a light guiding element, at least two light sensing elements and a processing unit. The light sensing elements have an offset therebetween along a first direction and a second direction and are configured to detect the light of the light source reflected by the object in a space range in front of the light source and passing through the light guiding element. The processing unit identifies the motion of the object along the optical axis according to an intensity variation of the light reflected by the object and detected by the light sensing elements.

The present invention further provides a movement detection device configured to detect a motion of an object. The movement detection device includes a light source, a light guiding element, a light sensing element and a processing unit. The light sensing element is configured to detect the light of the light source reflected by the object in a space range in front of the light source and passing through the light guiding element. The processing unit identifies the motion of the object according to an intensity variation of the light reflected by the object and detected by the light sensing element and to a number of times that the object appears in the space range within a predetermined time interval.

In the movement detection device of the present invention, the light source emits the light at an emission angle, and a detectable space range is determined according to the emission angle, a distance between the farthest ends of the light sensing elements and a space relationship between the light source and the light guiding element.

BRIEF DESCRIPTION OF THE DRAWINGS

Other objects, advantages, and novel features of the present invention will become more apparent from the following detailed description when taken in conjunction with the accompanying drawings.

DETAILED DESCRIPTION OF THE EMBODIMENT

The present invention will be described in connection with embodiments hereinafter which relates to a movement detection device including a light source, a light guiding element and at least two light sensing elements. When an object is moving along a transverse direction with respect to the movement detection device, the object will sequentially and gradually reflect the light to the light sensing elements and accordingly a movement along the transverse direction can be identified. When the object is moving along a longitudinal direction with respect to the movement detection device, the light sensing elements may detect an intensity variation of the light reflected by the object and accordingly a movement along the longitudinal direction can be identified. However, embodiments of the present invention are not to limit the present invention to any specific environment, application or particular implementation as described therein. Therefore, illustrations of the embodiments are only for interpretation rather than limitation of the present invention. It should be noted that in the embodiments and drawings hereinafter, elements that are not directly related to the present invention are omitted, and for illustration purpose the size relationship between elements are drawn slightly exaggerated.

Figure 1:
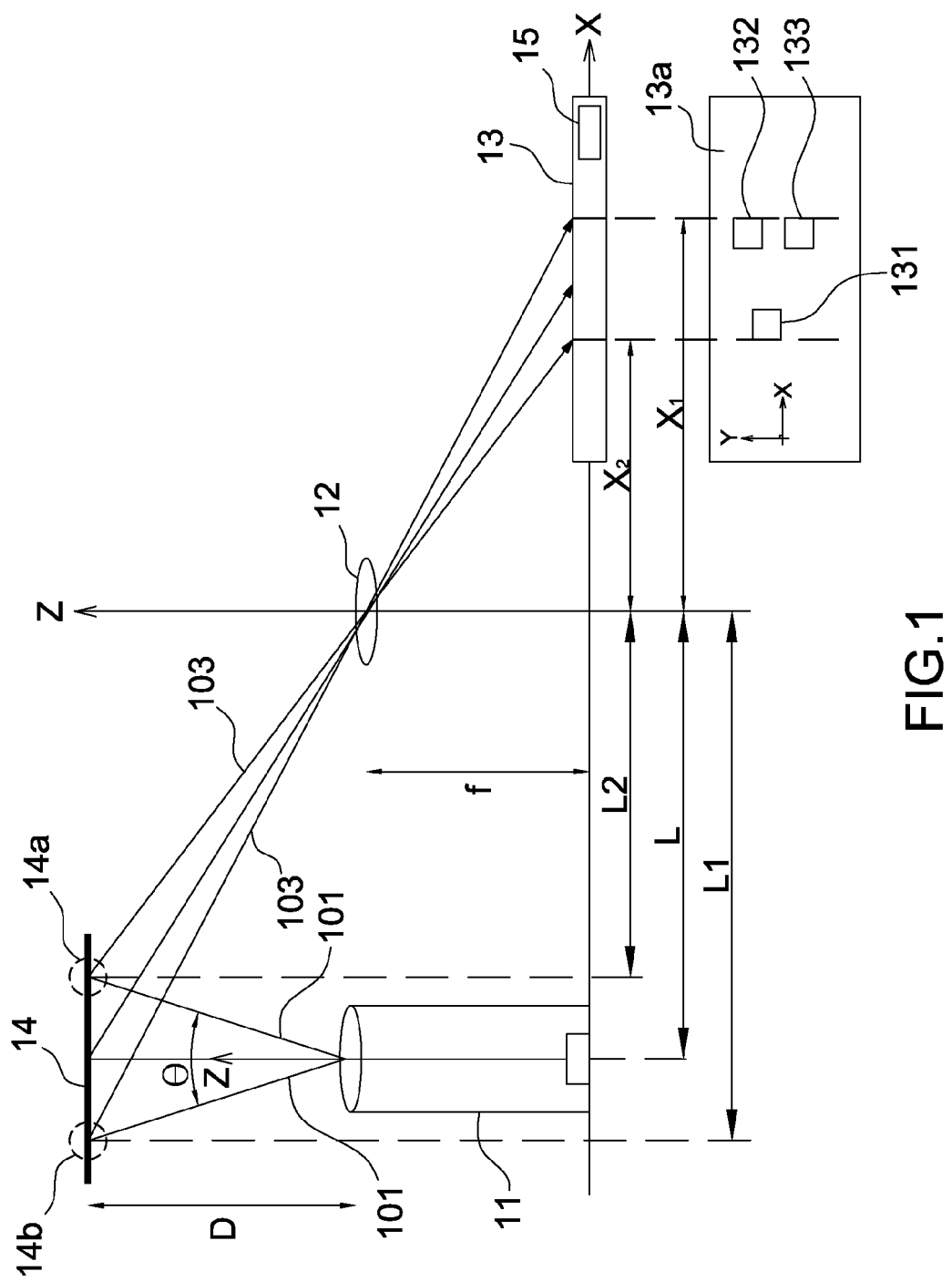
FIG. 1 shows a schematic diagram of the movement detection device according to the first embodiment of the present invention.

FIG. 1 shows a schematic diagram of the movement detection device according to the first embodiment of the present invention including a light source 11, a light guiding element 12, a sensing device 13 and a processing unit 15, which may be included in the sensing device 13 or independent therefrom. The light source 11 in this embodiment is exemplified by an infrared light source for illustration. The light guiding element 12 in this embodiment is exemplified by a lens for illustration. In this embodiment, the sensing device 13 includes three light sensing elements 131, 132 and 133, but the number of the light sensing elements is not to limit the present invention. A top view layout 13a of the sensing device 13 is also shown in FIG. 1 for illustrating a distribution of the light sensing elements 131, 132 and 133 in this embodiment. The processing unit 15 is electrically coupled to the light sensing elements 131, 132 and 133 for identifying a motion of the object according to the electric signals sent therefrom.

In this embodiment, an optical axis of the light source 11 emitting the light is defined as Z-axis and the light source 11 emits the light at an emission angle θ. When an object 14 is located at the emission direction, i.e. in front of the light source 11, a light beam 101 emitted from the light source 11 will project on a surface of the object 14, and the light will be reflected by the object 14 due to the texture and material of its surface and a part of the reflected light 103 will project on the sensing device 13 after passing through the light guiding element 12. It is appreciated from FIG. 1 that, when the object 14 is at a height D, the light reflected by the object 14 will pass through the light guiding element 14 and form a detectable area on the sensing device 13. Details of the detection method of the present invention will be illustrated hereinafter.

The light guiding element 12 of this embodiment may be a lens having a focus distance f. Assuming a distance between the center of the light guiding element 12 and one end 14a of a detectable region for detecting the object 14 is L2, and a distance between the center of the light guiding element 12 and the other end 14b (far end with respect to the light guiding element 12) of the detectable region is L1, and a distance between the center of the light guiding element 12 and the center of the light source 11 is L. In addition, assuming a distance between a front end of the light source 11 and the object 14 is D, and a transverse direction of the disposition of the light source 11, the light guiding element 12 and the sensing device 13 is X-direction. Accordingly, two equations can be obtained according to trigonometric functions:

$$L1 = L + D \times \tan(\theta/2) \quad \text{equation 1; and}$$

$$L2 = L - D \times \tan(\theta/2) \quad \text{equation 2}$$

Assuming a distance between a projecting position of the reflected light 103 from the point 14b on the sensing device 13 and the light guiding element 12 along the X-direction is X1, and a distance between a projecting position of the reflected light 103 from the point 14a on the sensing device 13 and the light guiding element 12 along the X-direction is X2. Accordingly, two equations can further be derived from equations 1 and 2:

$$(D/L1) = (f/X1) \quad \text{equation 3; and}$$

$$(D/L2) = (f/X2) \quad \text{equation 4}$$

In this way, a space relationship between the locations of the light sensing elements 131 to 133 should be disposed and the light guiding element 12 can be derived according to the information D, L1, L2 and f that are already known. In other words, a space range in which the object 14 should be operated can be determined according to the emission angle θ of the light source 11, a layout of the light sensing elements 131 to 133 and a space relationship between the light source 11 and the light guiding element 12. In this manner, the light sensing elements 131 to 133 may sequentially detect the variation of the reflected light 103 reflected by the object 14 when the object 14 is moving along the X-direction at aforementioned height (i.e. D), and the processing unit 15 identifies a sequence that the light sensing elements 131 to 133 detect the reflected light to identify the movement of the object 14 along the X-direction. Similarly, the method for identifying the movement of the object 14 along the Y-direction is identical to that along the X-direction. Detailed operation will be illustrated hereinafter.

Similarly, referring to the top view layout 13a, locations of the light sensing elements 131 to 133 have to be disposed are to make the light sensing element 133 in combination with the light sensing element 132 and/or 131 be able to simultaneously detect a movement along the X-direction and a Y-direction, wherein the Y-direction is a direction perpendicular to the X-direction on the top view layout 13a. For example, the light sensing elements 132 and 133 have no offset therebetween along the X-direction but have an offset therebetween along the Y-direction. The light sensing elements 132 and 133 respectively have an offset along the X-direction and the Y-direction with respect to the light sensing element 131. In this manner, the layout of the light sensing elements 131 and 132 or the layout of the light sensing elements 131 and 133 makes it possible to detect a movement on a plane perpendicular to the Z-direction, e.g. a movement along the X-direction. The layout of the light sensing elements 132 and 133 makes it possible to detect a movement on a plane perpendicular to the Z-direction, e.g. a movement along the Y-direction. In other words, when the sensing device 13 only needs to detect a movement of the object 14 in a single direction on the plane perpendicular to the Z-direction, only two light sensing elements are required. If a light sensing element having a higher sensibility is used to detect the distribution of the reflected light, a movement of the object on the plane (e.g. XY plane) perpendicular to the Z-direction can be identified by using only two light sensing elements.

Figure 2:
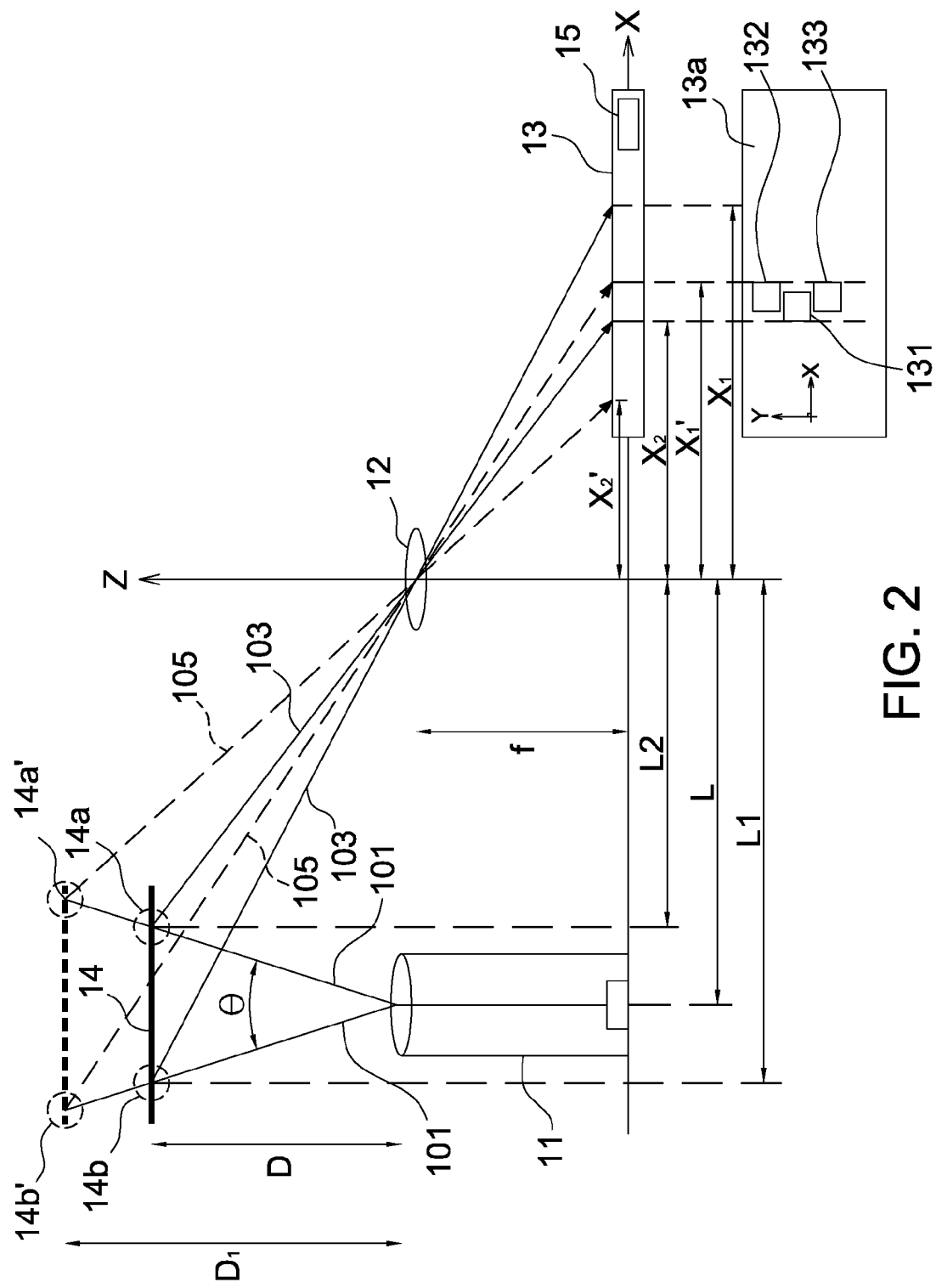
FIG. 2 shows a schematic diagram of the movement detection device according to the second embodiment of the present invention.

FIG. 2 shows a schematic diagram of the movement detection device according to the second embodiment of the present invention. The main difference between this embodiment and the first embodiment is in that, the movement detection device of the second embodiment defines a detectable range along the Z-direction in the space. For example, a detectable range for detecting the object 14 is a space range from D to D1, wherein D and D1 are distances between the front end of the light source 11 and the object 14. Therefore, one end 14a' and the other end 14b' (far end) of the detectable range for detecting the object 14 respectively reflect the light 105 and project on the position X2' and X1' on the sensing device 13, wherein X2' and X1' are transverse distances from the center of the light guiding element 12. In order to be able to detect the movement of the object 14 along the X-direction and the Y-direction when the object 14 is inside the space range D to D1, the boundary of the disposition of the light sensing elements 131 to 133 along the transverse direction should be limited by X2 and X1', such that the light sensing elements 131, 132 and/133 are able to detect the light reflected from at least a part of the object 14 inside the space range D to D1.

When the object 14 is moving along the Z-direction, because the intensity of the light projected on the sensing device 13 will change simultaneously, it is able to detect the motion of the object 14 along the Z-direction accordingly. For example, when the object 14 is moving from D toward D1, the intensity detected by the sensing device 13 decreases gradually; on the contrary, when the object 14 is moving from D1 toward D, the intensity detected by the sensing device 13 increases gradually. It is appreciated from FIG. 2 that, a detectable space range is determined according to a distance between X2 and X1', the emission angle θ of the light source 11 and a space relationship between the light source 11 and the light guiding element 12, and the detectable space range is a three-dimensional space defined by the X-direction, the Y-direction and the optical axis. For example, a distance between X2 and X1' may define a longitudinal detectable height (D1-D), and when the object 14 moves outside the longitudinal detectable height, the movement detection device is not able to detect the object 14. This feature makes the movement detection device of the present invention able to detect the motion of the object 14 along the longitudinal direction. For example, the processing unit 15 may identify the motion of the object 14 according to an intensity variation of the reflected light detected by the light sensing elements 131 to 133 and according to a number of times that the object 14 appears inside the space range within a predetermined time interval, wherein the predetermined time interval may be determined according to actual applications. In an embodiment, the processing unit 15 may identify a single click when identifying, for example, the intensity variation changing from dark to bright once and from bright to dark once within the predetermined time interval. In another embodiment, the processing unit 15 may identify a double click when identifying, for example, the intensity variation changing from dark to bright twice and from bright to dark twice within the predetermined time interval. However, the longitudinal motion of the object 14 that can be identified by the present invention is not limited to those mentioned above. In this way, the present invention is able to solve the problem of being unable to detect the longitudinal motion conventionally.

Comparing to the first embodiment, it can be found that a distance between X2 and X1' of FIG. 2 is smaller than that between X2 and X1 of FIG. 1. Therefore, for an object having a higher moving speed, as a distance between the light sensing elements 131 and 132 (or 133) is larger in the first embodiment, the device has a longer time interval to detect the movement of the object under the same hardware condition. Thus the movement detection device of the first embodiment has better performance in detecting fast moving object than that of the second embodiment. However, a space range that the movement detection device of the second embodiment can detect the movement of the object on a plane perpendicular to the Z-direction is between a height range D to D1; that is, as long as the object is located inside the height range D to D1, the sensing device 13 can detect not only the movement along the X-direction and the Y-direction thereby increasing the operation range, but also the movement along the Z-direction thereby increasing the practicability of the movement detection device, and thus the second embodiment is better than the first embodiment in this aspect. In this manner, a layout of the light sensing elements may be adjusted according to different applications.

Figure 3:
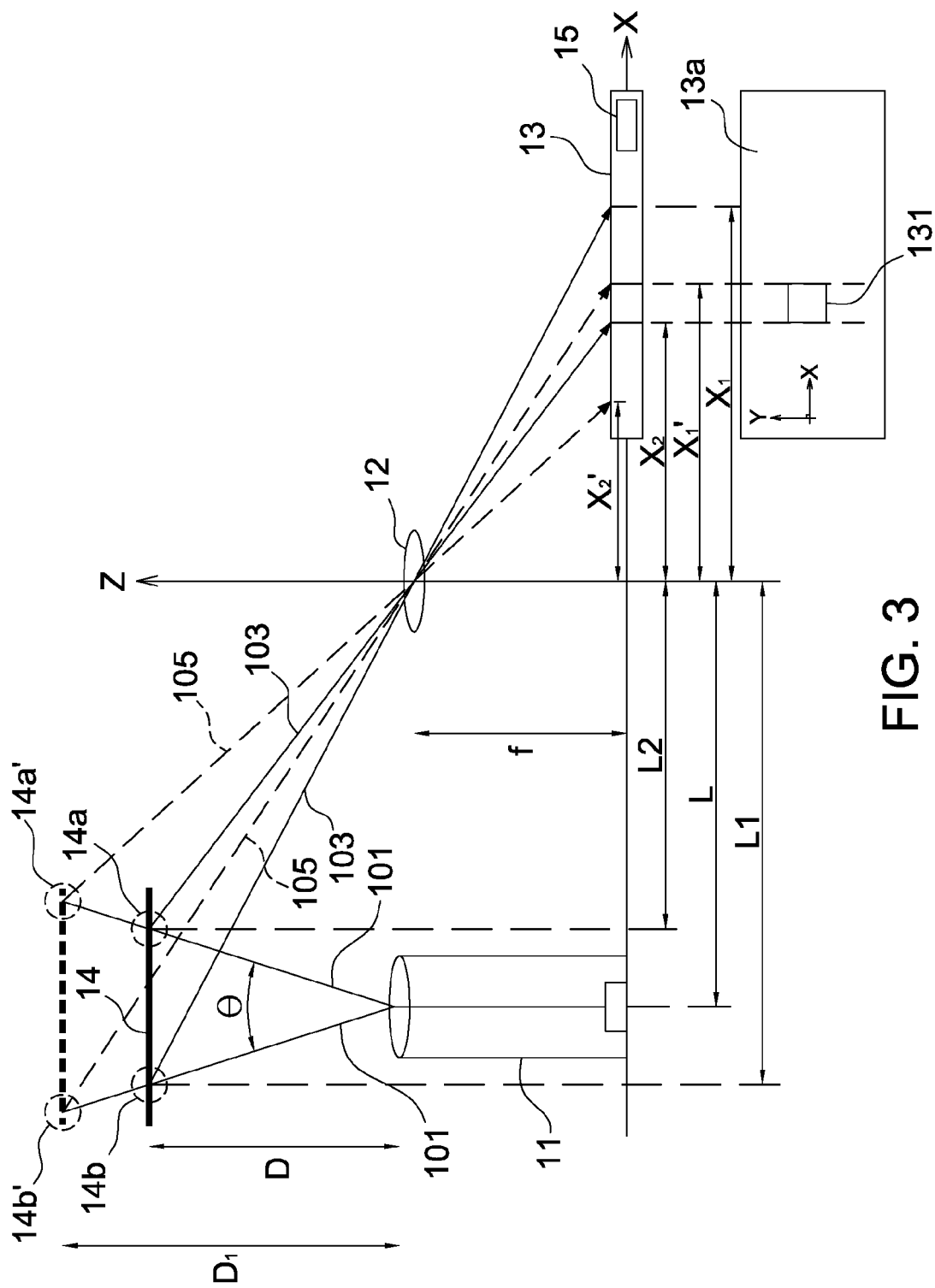
FIG. 3 shows a schematic diagram of the movement detection device according to an alternative embodiment of the present invention.

In addition, when it is desired to detect a longitudinal motion (e.g. a single click or double click) of the object with respect to the light source with the movement detection device of the present invention, disposing only one light sensing element as shown in FIG. 3 is also possible. The movement detection device in this embodiment includes a light source 11, a light guiding element 12, a sensing device 13 and a processing unit 15, wherein the sensing device 13 only includes one light sensing element 131. The processing unit 15 identifies the motion of the object 14 according to an intensity variation of the light reflected by the object 14 and a number of times that the object 14 appearing in a space range within a predetermined time interval detected by the light sensing element 131, similar to FIG. 2. In this embodiment, the space range may be determined according to the emission angle θ of the light source 11, a size of the light sensing element 131 and a space relationship (e.g. the distance L) between the light source 11 and the light guiding element 12.

Figure 4:
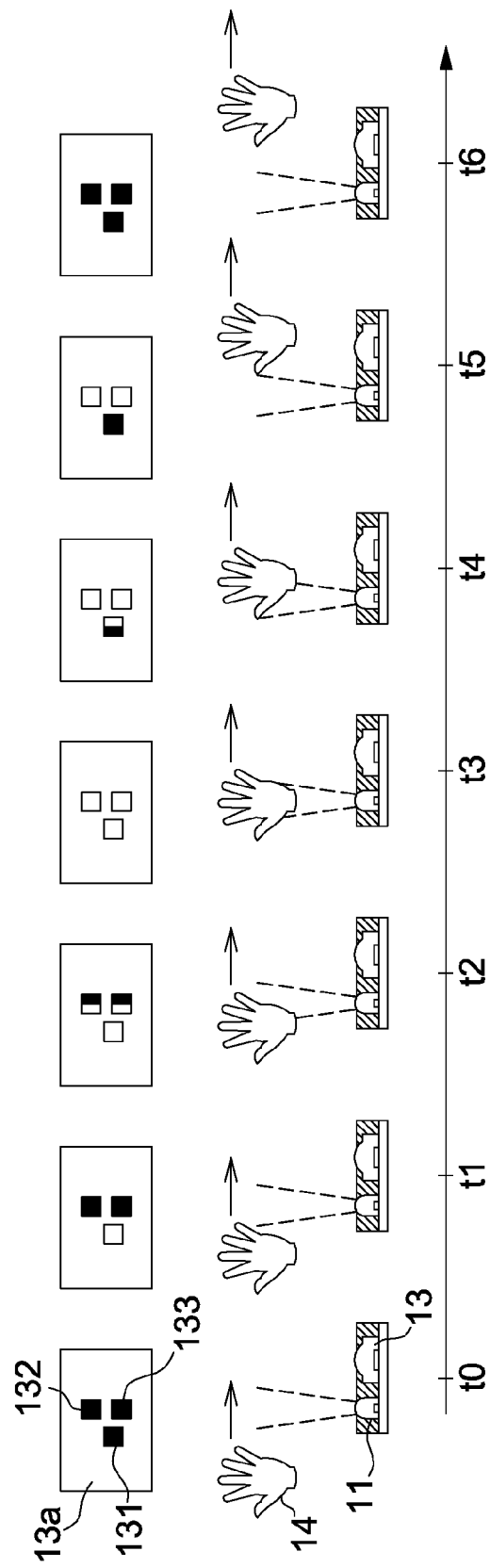
FIG. 4 shows a schematic diagram of the movement detection device of the present invention under continuous operation.

FIG. 4 further shows a schematic diagram of the sensing device of the present invention under continuous operation. The transverse axis represents time spots each denotes a relative position between the object 14 and the light sensing elements 131, 132 and 133. In this embodiment, a top view layout 13a of the light sensing elements 131, 132 and 133 is also shown for illustration.

At time t0, an object 14, such as the palm of a user herein, does not enter an emission angle of the light source 11 and thus the light sensing elements 131, 132 and 133 do not receive the light reflected by the object 14. Then at time t1, the object 14 starts to enter the emission angle of the light source 11 and thus the light sensing element 131 receives the reflected light (shown as a hollow square) but the light sensing elements 132 and 133 do not receive the reflected light (shown as solid squares). As time passing by, at time t2, the part of the object 14 entering the emission angle of the light source 11 increases and thus the light sensing elements 131, 132 and 133 all receive the reflected light, wherein the light sensing elements 132 and 133 only have a part receiving the reflected light. At time t3, the light reflected by the object 14 covers all the light sensing elements 131, 132 and 133. And then the object 14 starts to gradually leave the emission angle of the light source 11. At time t4, a part of the light sensing element 131 does not receive the reflected light. At time t5, only the light sensing elements 132 and 133 can receive the reflected light. At time t6, as the object 14 totally leaves the emission angle of the light source 11, the light sensing elements 131, 132 and 133 come to a status without receiving any reflected light. The light sensing elements 131 to 133 generate electric signals after receiving the reflected light and the sensing device 13 identifies a moving direction of the object according to the electric signals received. It is appreciated that the method that the sensing device 13 identifies the movement of an object in both directions on a plane is similar to that shown in FIG. 3.

Furthermore, in the above embodiments the light sensing elements 131, 132 and 133 can detect a distribution of the reflected light and thus can be adopted in the case properly disposing only two light sensing elements. For example, by using a layout of the light sensing elements 131 and 132 or the light sensing element 131 and 133 having an offset from each other of the present invention, the movement of the object 14 along a single direction can be identified. In addition, although the basic operation effect is influenced by disposing more light sensing elements, the sensing performance can be increased.

In the aforementioned embodiments, although the light guiding element 12 is shown by a lens, it is only to emphasize the effect of focusing the reflected light 103 on the sensing device 13 when the reflected light 103 passes through the light guiding element 12. In other embodiment, if the light guiding element 12 is an element with a tiny pinhole, the reflected lights 103 and 105 can still be projected on the sensing device 13. Through corresponding modification, it is able to modify the disposition of the light sensing elements; however, the disposition of the light sensing elements should still be limited by the aforementioned boundary condition.

It is appreciated from the above embodiments that an important feature of the present invention is to detect the variation of the reflected light with a plurality of light sensing elements at different time spots and the detected variation is served as a basis to identify the moving direction of an object. And an identification result of the moving direction may be used to trigger a specific command based on the movement of the object so as to accordingly perform a post-processing and/or control mechanism according to the command. For example, the movement detection device of the present invention may be adopted in a portable device such as a note book, a cell phone; and it also may be adopted in a desktop device such as a TV, a PC or a game machine. When the detecting function is enabled, it is able to trigger a specific command by a body motion or object movement. For example, when the movement detection device is applied in a note book, it is able to flip photos with gestures when reviewing photos or to roll pages with gestures when editing files or browsing web pages. But these applications are not to limit the present invention.

Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. A movement detection device configured to detect a movement of an object in a space range, the movement detection device comprising:
    a light source configured to emit light along an optical axis;
    a light guiding element;
    at least two light sensing elements laid out on a surface of a same substrate and having an offset therebetween along a first direction such that the object, when moving in the space range, reflects the light from the light source sequentially to the light sensing elements through the light guiding element; and
    a processing unit configured to
        identify the movement of the object along the first direction according to a sequence in which the light sensing elements detect light reflected by the object,
        identify a motion of the object along the optical axis according to an intensity variation of the light reflected by the object and detected by the light sensing elements, and
        identify a single click when the intensity variation detected within a predetermined time interval changes from dark to bright once and from bright to dark once.

2. The movement detection device as claimed in claim 1, wherein the light guiding element is a lens or an element having a pinhole.

3. The movement detection device as claimed in claim 1, wherein
    the light source is configured to emit the light at an emission angle, and
    the space range is determined according to the emission angle, a layout of the light sensing elements and a space relationship between the light source and the light guiding element.

4. The movement detection device as claimed in claim 1, comprising a first light sensing element, a second light sensing element and a third light sensing element, the first light sensing element and the second light sensing element having no offset therebetween along a first direction and having an offset therebetween along a second direction, the first light sensing element and the second light sensing element respectively having an offset along the first direction and the second direction with respect to the third light sensing element, wherein the first direction is perpendicular to the second direction.

5. The movement detection device as claimed in claim 1, wherein the processing unit is configured to identify the motion of the object according to a number of times that the object appears in the space range within a predetermined time interval.

6. The movement detection device as claimed in claim 1, wherein the processing unit is further configured to identify a double click when the intensity variation detected within another predetermined time interval changes from dark to bright and from bright to dark twice.

7. The movement detection device as claimed in claim 4, wherein the processing unit is configured to identify the movement of the object along the first direction and the second direction according to a sequence in which the first light sensing element, the second light sensing element and the third light sensing element detect the light reflected by the object.

8. The movement detection device as claimed in claim 4, wherein the space range is a three-dimensional space defined by the first direction, the second direction and the optical axis.

9. A movement detection device configured to detect a movement of an object in a space range, the movement detection device comprising:
    a light source configured to emit light along an optical axis;
    a light guiding element;
    at least two light sensing elements laid out on a surface of a same substrate and having an offset therebetween along a first direction such that the object, when moving in the space range, reflects the light from the light source sequentially to the light sensing elements through the light guiding element; and
    a processing unit configured to identify the movement of the object along the first direction according to a sequence in which the light sensing elements detect light reflected by the object, identify a motion of the object along the optical axis according to an intensity variation of the light reflected by the object and detected by the light sensing elements, and identify a double click when the intensity variation detected within a predetermined time interval changes from dark to bright and from bright to dark twice.

10. The movement detection device as claimed in claim 9, wherein the light guiding element is a lens or an element having a pinhole.

11. The movement detection device as claimed in claim 9, wherein the light source is configured to emit the light at an emission angle, and the space range is determined according to the emission angle, a layout of the light sensing elements and a space relationship between the light source and the light guiding element.

12. The movement detection device as claimed in claim 9, comprising a first light sensing element, a second light sensing element and a third light sensing element, the first light sensing element and the second light sensing element having no offset therebetween along a first direction and having an offset therebetween along a second direction, the first light sensing element and the second light sensing element respectively having an offset along the first direction and the second direction with respect to the third light sensing element, wherein the first direction is perpendicular to the second direction.

13. The movement detection device as claimed in claim 12, wherein the processing unit is configured to identify the movement of the object along the first direction and the second direction according to a sequence in which the first light sensing element, the second light sensing element and the third light sensing element detect the light reflected by the object.

14. The movement detection device as claimed in claim 12, wherein the space range is a three-dimensional space defined by the first direction, the second direction and the optical axis.

* * * * *